US012251542B2

(12) United States Patent
Schader et al.

(10) Patent No.: US 12,251,542 B2
(45) Date of Patent: Mar. 18, 2025

(54) MEDICAMENT DELIVERY DEVICE

(71) Applicant: Sanofi-Aventis Deutschland GmbH, Frankfurt am Main (DE)

(72) Inventors: Marc Schader, Frankfurt am Main (DE); Michael Helmer, Frankfurt am Main (DE); Winfried Huthmacher, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 208 days.

(21) Appl. No.: 17/401,573

(22) Filed: Aug. 13, 2021

(65) Prior Publication Data

US 2021/0369977 A1 Dec. 2, 2021

Related U.S. Application Data

(63) Continuation of application No. 15/778,348, filed as application No. PCT/EP2016/078271 on Nov. 21, 2016, now Pat. No. 11,097,064.

(30) Foreign Application Priority Data

Nov. 27, 2015 (EP) .................................... 15196705

(51) Int. Cl.
*A61M 5/32* (2006.01)
*A61M 5/20* (2006.01)
*A61M 5/24* (2006.01)

(52) U.S. Cl.
CPC ........ *A61M 5/3204* (2013.01); *A61M 5/2033* (2013.01); *A61M 5/2422* (2013.01);
(Continued)

(58) Field of Classification Search
CPC ...... A61M 5/3202; A61M 5/321; A61M 5/24; A61M 5/2033; A61M 5/20; A61M 5/348;
(Continued)

(56) References Cited

U.S. PATENT DOCUMENTS 4,976,701 A 12/1990 Ejlersen et al.
5,098,400 A 3/1992 Crouse et al.
(Continued)

FOREIGN PATENT DOCUMENTS

CN 101854965 10/2010
CN 101868275 10/2010
(Continued)

OTHER PUBLICATIONS

International Preliminary Report on Patentability in International Appln. No. PCT/EP2016/078271, dated May 29, 2018, 7 pages.
(Continued)

*Primary Examiner* — Emily L Schmidt
*Assistant Examiner* — Antarius S Daniel
(74) *Attorney, Agent, or Firm* — Bond, Schoeneck & King, PLLC

(57) ABSTRACT

The present disclosure relates to a medicament delivery device including a cartridge holder to which an injection needle holder can be fixed, the injection needle holder holding an injection needle having a proximal end and a distal end, the proximal end being protected by an inner injection needle cap detachably connected to the injection needle holder, the cartridge holder being mounted in a housing and configured to receive a cartridge of medicament, a cap assembly detachably connected to the housing, and a gripping mechanism configured to remove the inner injection needle cap from the injection needle holder when the cap assembly is pulled away from the cartridge holder.

19 Claims, 6 Drawing Sheets

(52) U.S. Cl.
CPC ... *A61M 5/2466* (2013.01); *A61M 2005/2013* (2013.01); *A61M 2005/206* (2013.01); *A61M 2005/2073* (2013.01); *A61M 2005/2474* (2013.01); *A61M 5/3202* (2013.01)

(58) Field of Classification Search
CPC .... A61M 5/34; A61M 5/2455; A61M 5/3213; A61M 5/3216; A61M 2005/1585; A61M 2005/206; A61M 2005/2474; A61M 2005/312
See application file for complete search history.

(56) References Cited

U.S. PATENT DOCUMENTS

| | | | |
|---|---|---|---|
| 5,273,544 A | | 12/1993 | Van Der Wal |
| 5,928,205 A | | 7/1999 | Marshall |
| 8,708,968 B2 | * | 4/2014 | Julian ............... A61M 5/3204 604/192 |
| 2005/0027259 A1 | * | 2/2005 | Vetter ............... A61M 5/001 604/192 |
| 2011/0077615 A1 | | 3/2011 | Schraga |
| 2013/0274671 A1 | | 10/2013 | Jennings et al. |
| 2014/0243753 A1 | | 8/2014 | Bostrom |
| 2015/0196718 A1 | | 7/2015 | Radmer et al. |
| 2015/0202379 A1 | | 7/2015 | Raday et al. |

FOREIGN PATENT DOCUMENTS

| | | |
|---|---|---|
| CN | 103764207 | 4/2014 |
| CN | 103945881 | 7/2014 |
| CN | 104394924 | 3/2015 |
| JP | H11-502448 | 3/1999 |
| JP | 2013-539701 | 10/2013 |
| JP | 2014-506159 | 3/2014 |
| JP | 2015-513439 | 5/2015 |
| JP | 2016-538056 | 12/2016 |
| JP | 2016-538058 | 12/2016 |
| WO | WO 1996/030065 | 10/1996 |
| WO | WO 2009/040601 | 4/2009 |
| WO | WO 2009/040605 | 4/2009 |
| WO | WO 2012/049147 | 4/2012 |
| WO | WO 2012/085029 | 6/2012 |
| WO | WO 2013/048310 | 4/2013 |
| WO | WO 2013/135566 | 9/2013 |
| WO | WO 2014/154498 | 10/2014 |
| WO | WO 2015/078866 | 6/2015 |
| WO | WO 2015/078868 | 6/2015 |
| WO | WO 2015/118550 | 8/2015 |

OTHER PUBLICATIONS

International Search Report and Written Opinion in International Appln. No. PCT/EP2016/078271, mailed Oct. 2, 2017, 10 pages.

* cited by examiner

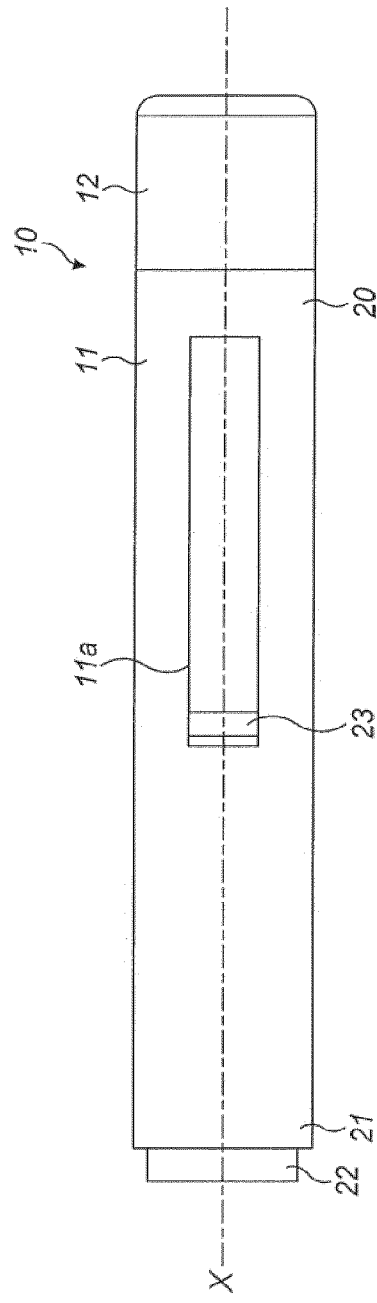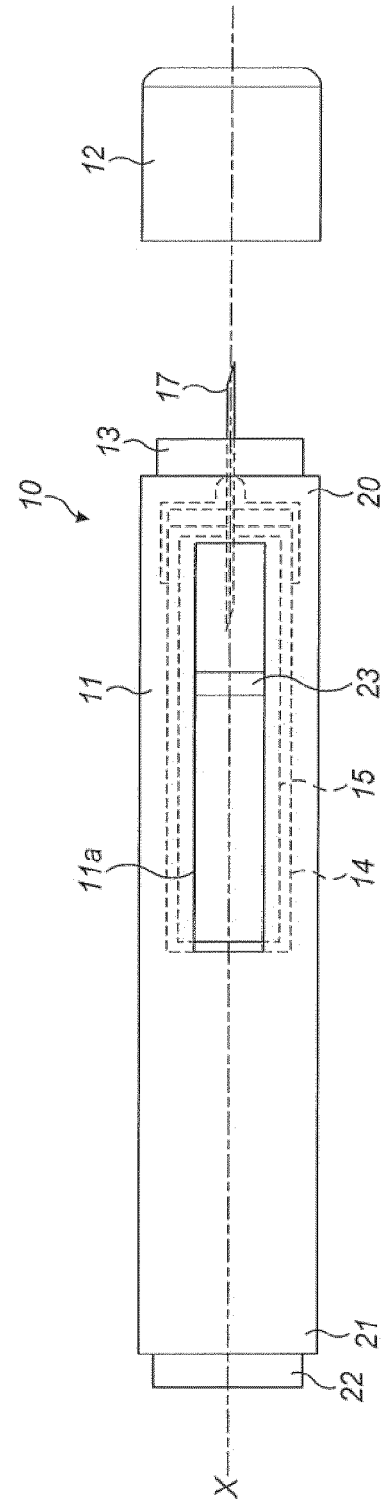

MEDICAMENT DELIVERY DEVICE

CROSS REFERENCE TO RELATED APPLICATIONS

The present application is a continuation of patent application Ser. No. 15/778,348, filed on May 23, 2018, which is the national stage entry of International Patent Application No. PCT/EP2016/078271, filed on Nov. 21, 2016, and claims priority to Application No. EP 15196705.6, filed on Nov. 27, 2015, the disclosures of which are expressly incorporated herein in entirety by reference thereto.

TECHNICAL FIELD

The present disclosure relates to a device for delivery of medicament to a patient.

BACKGROUND

Medicament injection devices such as auto-injectors are a common type of medicament delivery devices designed to deliver a medicament by injection. This type of devices are designed to be easy to use and intended for self-administration by patients, or administration by persons having no formal medical training.

In some circumstances, medicament injection devices are used by patients of impaired physical ability such as the elderly or physically impaired, and it may be harder for them to operate the device.

At least in certain embodiments, the present disclosure sets out to overcome or ameliorate at least some of the problems mentioned above. In particular, the present disclosure sets out to provide a device for delivery of medicament which is easy to use.

SUMMARY

Aspects of the present disclosure relate to a device for delivery of medicament to a patient.

According to a further aspect of the present disclosure, there is provided a medicament delivery device comprising:
- a cartridge holder to which an injection needle holder can be fixed, the injection needle holder holding an injection needle having a proximal end and a distal end, the proximal end being protected by an inner injection needle cap detachably connected to the injection needle holder, the cartridge holder being mounted in a housing and configured to receive a cartridge of medicament;
- a cap assembly detachably connected to the housing; and
- a gripping mechanism configured to remove the inner injection needle cap from the injection needle holder when the cap assembly is pulled away from the cartridge holder. This may advantageously reduce the amount of steps a user must perform for a medicament injection procedure. Conventional medicament delivery devices require the user to remove the cap assembly and the inner needle cap separately to expose the needle in order to make the device ready for injection. It shall be appreciated that infirm patients such as the elderly or physically impaired may find removing the inner needle cap more difficult than removing the cap assembly due to the small size of the inner needle cap. According to the present disclosure, both the cap assembly and the inner needle cap are removed simultaneously in a single operation, which thereby makes the medicament delivery device easier to use.

The cap assembly may be configured to pull the inner injection needle cap away from the injection needle holder in an axial direction along a longitudinal axis of the housing when the cap assembly is pulled away from the cartridge holder. This may advantageously ensure that the inner needle cap is easily removable from the injection needle holder.

The gripping mechanism may comprise at least one gripping member movable from a retracted position towards an engaged position in which the or each gripping member engages the inner injection needle cap, and the or each gripping member may move from the retracted position towards the engaged position when the cap assembly is pulled away from the cartridge holder. In one embodiment, said at least one gripping member is moveable relative to the cap assembly from the retracted position towards the engaged position.

The gripping mechanism may comprise a catch configured to hold the inner injection needle cap and remove the inner injection needle cap from the injection needle holder while the cap assembly is pulled away from the cartridge holder. This may advantageously ensure that the inner injection needle cap is removed in a reliable way from the housing prior injection.

The gripping mechanism may comprise a plurality of spring arms each having a free end, and the spring arms may be configured such that the free ends fold on and clamp the inner injection needle cap when the cap assembly is pulled away from the cartridge holder. This may advantageously provide a medicament delivery device which is of simple construction.

In the retracted position, the free end of each spring arm may rest on the cartridge holder, and in the engaged position, the free end of each spring arm may clamp the inner injection needle cap.

The spring arms may biased towards each other.

The cap assembly may comprise an inner cap and an outer cap connected to the inner cap, the spring arms may have a first end opposed to the free end and each first end may be secured to the inner cap.

An outer needle cap may be located over the inner needle cap and the cap assembly may comprise a stop member, the stop member being configured to engage a distal section of the outer needle cap to remove the outer needle cap from the inner needle cap prior the removal of the inner needle cap from the injection needle holder when the cap assembly is pulled away from the cartridge holder. Both the inner needle cap and the outer needle cap are removed from the injection needle holder in a single operation, which thereby reduces the amount of steps a user must perform for a medicament injection procedure.

The first end of each spring arm may be secured to the stop member.

The medicament delivery device may comprise a pair of spring arms facing each other.

The medicament delivery device may comprise an injection needle holder to which an injection needle is fixed, the injection needle having a proximal end and a distal end, the proximal end being protected by an inner injection needle cap detachably connected to the injection needle holder.

The medicament delivery device may comprise a cartridge of medicament, the cartridge being received in the cartridge holder.

According to a further aspect of the present disclosure, there is provided a method of removing an inner injection needle cap from an injection needle holder holding an injection needle in a medicament delivery device, the injection needle having a proximal end and a distal end, the proximal end being protected by the inner injection needle cap, the medicament delivery device comprising:

a cartridge holder to which the injection needle holder can be fixed, the cartridge holder being mounted in a housing and configured to receive a cartridge of medicament;

a cap assembly detachably connected to the housing; and a gripping mechanism;

wherein the method comprises pulling the cap assembly away from the cartridge holder to cause the gripping mechanism to remove the inner injection needle cap from the injection needle holder.

An outer needle cap may be located over the inner needle cap and the method may comprise pulling the cap assembly away from the cartridge holder to cause the outer needle cap to be pulled away from the inner injection needle cap.

According to a further aspect of the present disclosure, there is provided a method of removing an inner injection needle cap from an injection needle in a medicament delivery device, the method comprising moving a cap assembly of the medicament delivery device a predetermined distance in a proximal direction to remove the cap assembly and the inner injection needle cap from the device.

An outer needle cap may be located over the inner needle cap and moving the cap assembly the predetermined distance may cause the outer needle cap to be removed from the inner injection needle cap.

The terms "drug" or "medicament" which are used interchangeably herein, mean a pharmaceutical formulation that includes at least one pharmaceutically active compound.

The term "medicament delivery device" shall be understood to encompass any type of device, system or apparatus designed to immediately dispense a drug to a human or non-human body (veterinary applications are clearly contemplated by the present disclosure). By "immediately dispense" is meant an absence of any necessary intermediate manipulation of the drug by a user between discharge of the drug from the drug delivery device and administration to the human or non-human body. Without limitation, typical examples of drug delivery devices may be found in injection devices, inhalers, and stomach tube feeding systems. Again without limitation, exemplary injection devices may include, e.g., syringes, autoinjectors, injection pen devices and spinal injection systems."

BRIEF DESCRIPTION OF THE DRAWINGS

Exemplary embodiments of the present disclosure are described with reference to the accompanying drawings, in which:

FIGS. 1A and 1B show schematic side views of a medicament delivery device according to an embodiment of the present disclosure;

DETAILED DESCRIPTION

Figure 2:
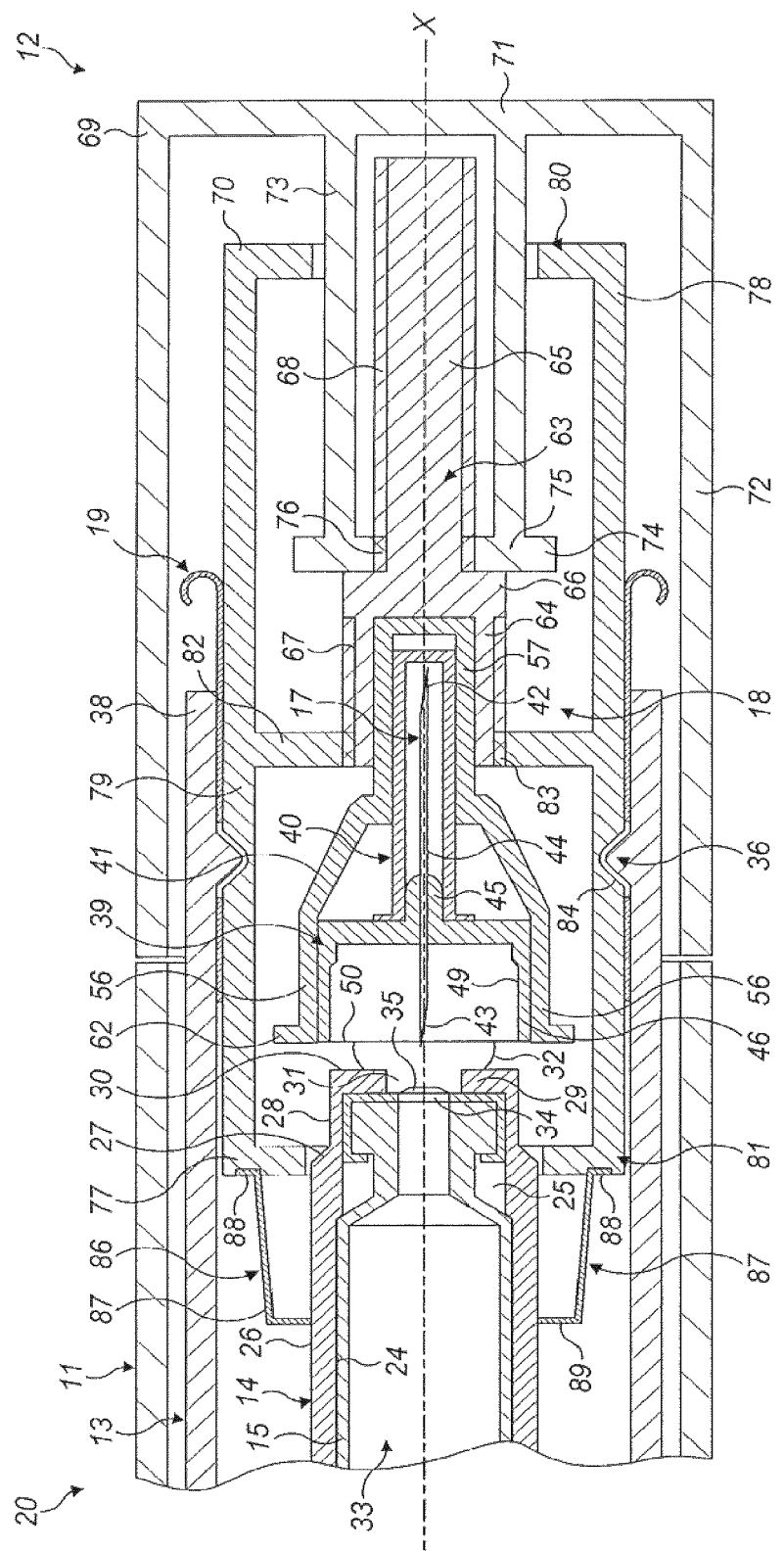
FIG. 2 shows a cross-sectional view of a part of the medicament delivery device of FIG. 1A, the needle being in a storage position.

Embodiments of the disclosure provide a mechanism for removing the inner needle cap from an injection needle holder of a medicament delivery device when the cap assembly of the medicament delivery device is pulled away from the cartridge holder. Providing such a mechanism allows both the cap assembly and the inner needle cap to be removed simultaneously in a single operation, which thereby makes the medicament delivery device easier to use.

According to some embodiments of the present disclosure, an exemplary drug delivery device 10, herein simply referred to as "device 10", is shown in FIGS. 1A & 1B.

The terms "proximal" and "distal" herein respectively refer to as relatively closer to the patient and relatively further away from the patient.

The drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Device 10, as described above, is configured to inject a medicament, e.g. a liquid medicament, into a patient's body. Device 10 includes a body or housing 11 which typically contains a reservoir containing the medicament to be injected (e.g., a syringe) and the components required to facilitate one or more steps of the delivery process. Device 10 can also include a cap assembly 12 that can be detachably mounted to the housing 11. Typically a user must remove the cap assembly 12 from the housing 11 before the device 10 can be operated.

The device 10 includes a cartridge 15 pre-filled with liquid medicament, and a pen needle or needle assembly 16 (visible in FIG. 2) comprising an injection needle 17 for injecting medicament from the cartridge 15 to a patient's body. The housing 11 includes a window 11a, through which the contents of the cartridge 15 can be viewed. As shown in FIG. 2, the device 10 also comprises a coupling mechanism 18 connecting the cap assembly 12 to the needle assembly 16, and shield elements 19 for occluding access to the needle 17 when the device 10 is in use.

As shown, the housing 11 is substantially cylindrical and has a substantially constant diameter along the longitudinal axis X. The housing 11 has a proximal region 20 and a distal region 21. The term "proximal" refers to a location that is relatively closer to a site of injection, and the term "distal" refers to a location that is relatively further away from the injection site.

The device 10 can also include a needle sleeve 13 coupled to housing 11 to permit movement of sleeve 13 relative to housing 11. The sleeve 13 is retractably mounted in the housing 11. For example, sleeve 13 can move in a longitudinal direction parallel to longitudinal axis X. Specifically, movement of the sleeve 13 in a distal direction can permit the needle 17 to extend from the proximal region 20 of the housing 11.

Insertion of the needle 17 can occur via several mechanisms. For example, needle 17 may be fixedly located relative to housing 11 and initially be located within an extended needle sleeve 13. Distal movement of the sleeve 13 by placing a proximal end of the sleeve 13 against a patient's body and moving the housing 11 in a proximal direction will uncover the proximal end of the needle 17. Such relative movement allows the proximal end of the needle 17 to extend into the patient's body. Such insertion is termed "manual" insertion as needle 17 is manually inserted via the patient's manual movement of the housing 11 relative to the sleeve 13.

Another form of insertion is "automated," whereby needle 17 moves relative to housing 11. Such insertion can be triggered by movement of sleeve 13 or by another form of activation, such as, for example, a button 22. As shown in FIGS. 1A & 1B, button 22 is located at a distal end of housing 11. However, in other embodiments, button 22 could be located on a side of housing 11.

Other manual or automated features can include drug injection or needle retraction, or both. Injection is the process by which a bung or piston 23 is moved from a distal location within a cartridge to a more proximal location within the cartridge in order to force a medicament from the cartridge through needle 17. In some embodiments, a drive spring (not shown) is under compression before device 10 is activated. A distal end of the drive spring can be fixed within distal region 21 of housing 11, and a proximal end of the drive spring can be configured to apply a compressive force to a distal surface of piston 23. Following activation, at least part of the energy stored in the drive spring can be applied to the distal surface of piston 23. This compressive force can act on piston 23 to move it in a proximal direction. Such proximal movement acts to compress the liquid medicament within the cartridge, forcing it out of needle 17.

Following injection, needle 17 can be retracted within sleeve 13 or housing 11. Retraction can occur when sleeve 13 moves proximally as a user removes device 10 from a patient's body. This can occur as needle 17 remains fixedly located relative to housing 11. Once a proximal end of sleeve 13 has moved past a proximal end of needle 17, and needle 17 is covered, sleeve 13 can be locked. Such locking can include locking any distal movement of sleeve 13 relative to housing 11.

Another form of needle retraction can occur if needle 17 is moved relative to housing 11. Such movement can occur if the cartridge within housing 11 is moved in a distal direction relative to housing 11. This distal movement can be achieved by using a retraction spring (not shown), located in proximal region 20. A compressed retraction spring, when activated, can supply sufficient force to the cartridge to move it in a distal direction. Following sufficient retraction, any relative movement between needle 17 and housing 11 can be locked with a locking mechanism. In addition, button 22 or other components of device 10 can be locked as required.

As shown in FIG. 2, the cartridge holder 14 is securely mounted to the housing 11. The cartridge holder 14 comprises a wall 24 which defines a cavity 25 for receiving the cartridge 15. The cartridge holder 14 comprises a main portion 26 and a proximal portion 27. The main portion 26 is substantially cylindrical and has a substantially constant diameter along the longitudinal axis X. The proximal portion 27 is substantially cylindrical and has a diameter which is less than the diameter of the main portion 26. The proximal portion 27 includes an external thread 28. A rib 29 projects inwardly from the wall 24 at an end 30 of the proximal portion 27 and extends around the entire circumference of the proximal portion 27. The rib 29 defines an opening 31 through which the needle 17 locates during injection. A seal-cutter 32 is fixed to the rib 29. The seal-cutter 32 is in the form of a pair of cutting blades protruding from the rib 29 and distributed around the opening 31.

The cartridge 15 is in the form of a tubular container 33 which stores the liquid medicament to be injected to the patient's body. The container 33 is fitted securely within the cavity 25 of the cartridge holder 14. The container 33 includes an aperture 34 which faces the opening 31 of the cartridge holder 14 and which is sealed by means of a septum 35.

The sleeve 13 has a generally tubular shape and extends along the longitudinal axis X, between the housing 11 and the cartridge holder 14. The sleeve 13 is slidable along the longitudinal axis X between a deployed position in which the sleeve 13 protrudes from the proximal region 20 of the housing 11 and a retracted position in which the sleeve 13 is retracted within the housing 11. A circumferential notch 36 is provided on an internal surface of the sleeve 13 at a proximal extremity 38 of the sleeve 13. Rotation of the sleeve 13 relative to the housing 11 is prevented by a splined arrangement (not shown).

The needle assembly 16 comprises the injection needle 17, an injection needle holder 39 to which the needle 17 is fixed, an inner needle shield or inner needle cap 40 and an outer needle shield or outer needle cap 41.

Figure 3:
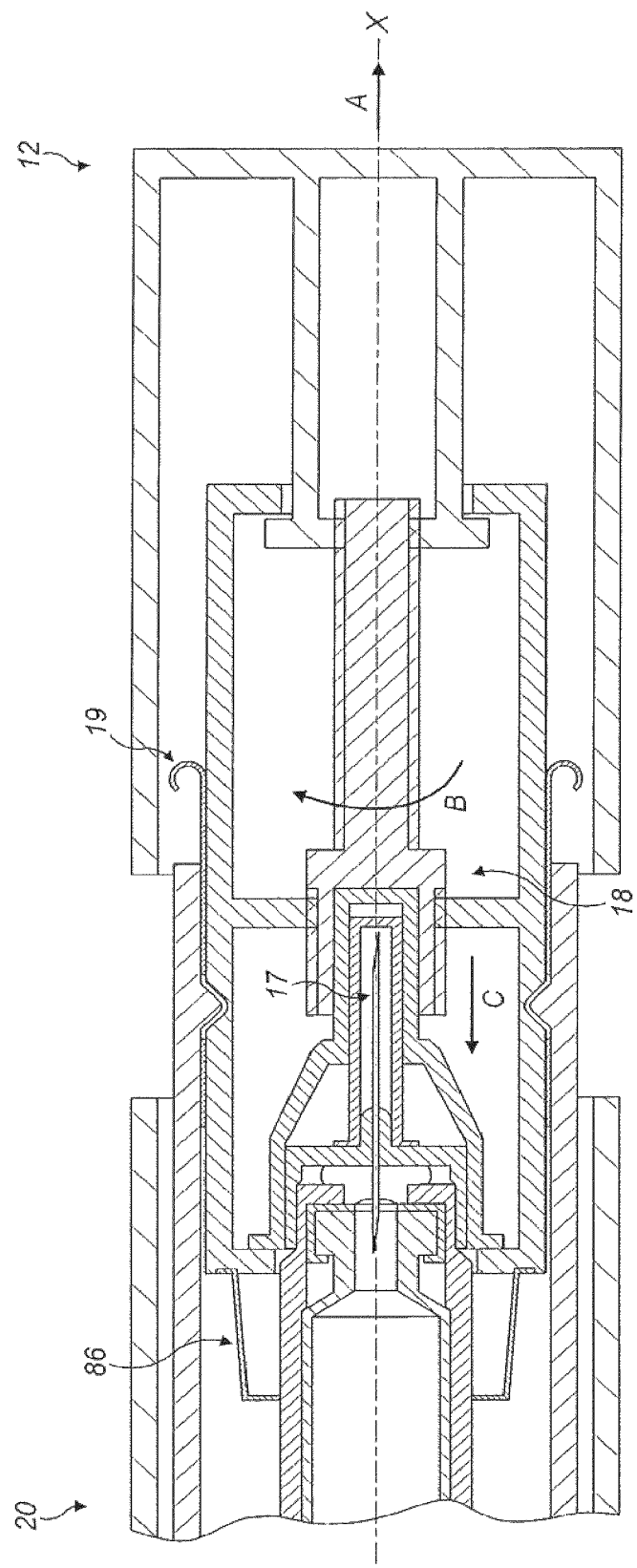
FIG. 3 shows a cross-sectional view of a part of the medicament delivery device of FIG. 1A, the needle being in a use position.
Figure 4:
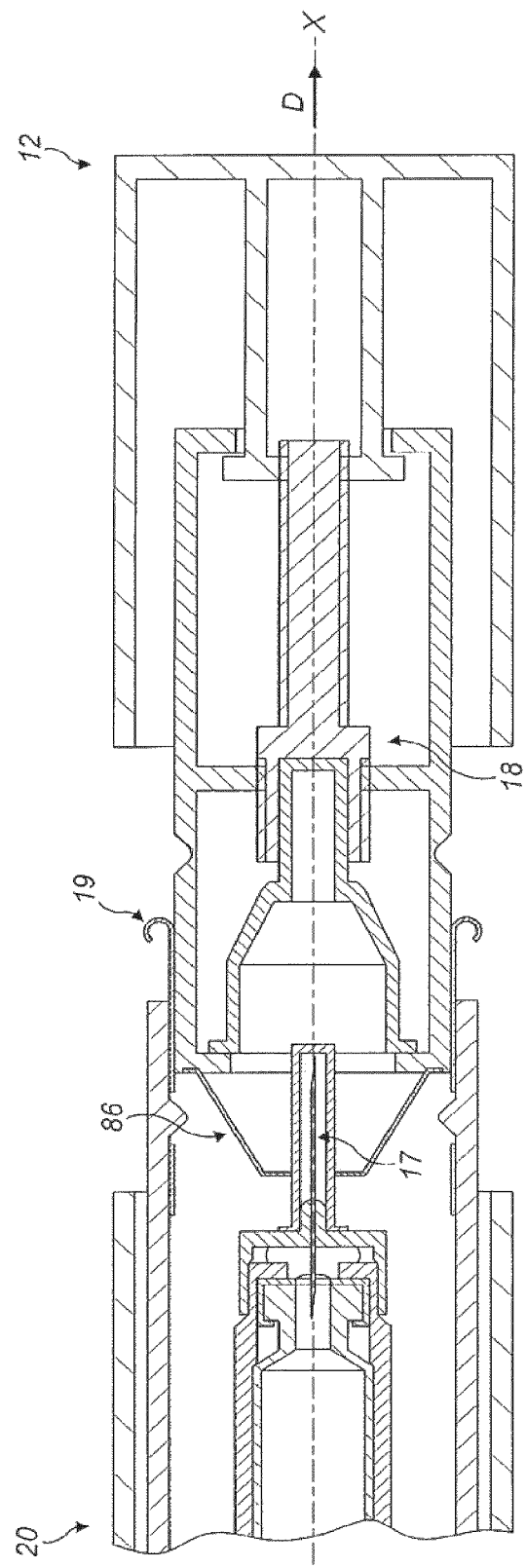
FIG. 4 shows a cross-sectional view of a part of the medicament delivery device of FIG. 1A, the needle being in the use position, the shield arms being held in an inactive position by the inner cap.
Figure 5:
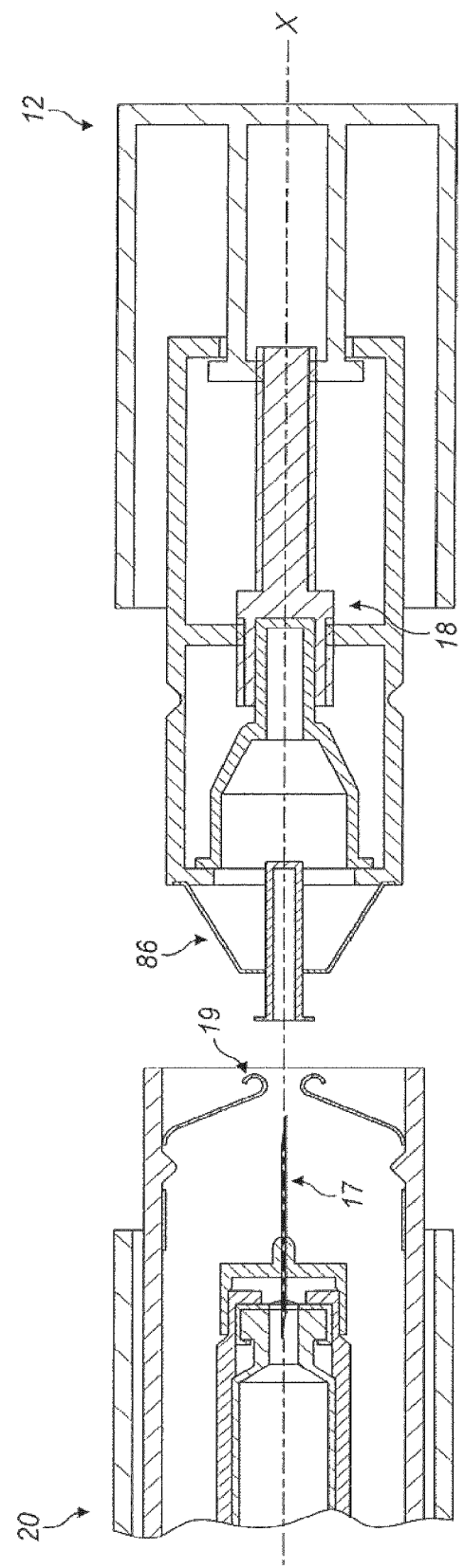
FIG. 5 shows a cross-sectional view of a part of the medicament delivery device of FIG. 1A, the needle being in the use position, the inner needle cap being removed from the needle and the shield arms being in a needle safe position.
Figure 6A:
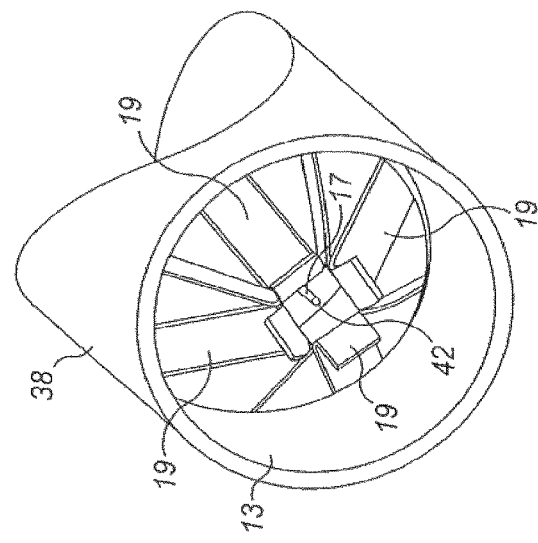
FIG. 6A shows a perspective view of a part of the medicament delivery device of FIG. 1A showing in greater detail the shield arms in an inactive position.
Figure 6B:
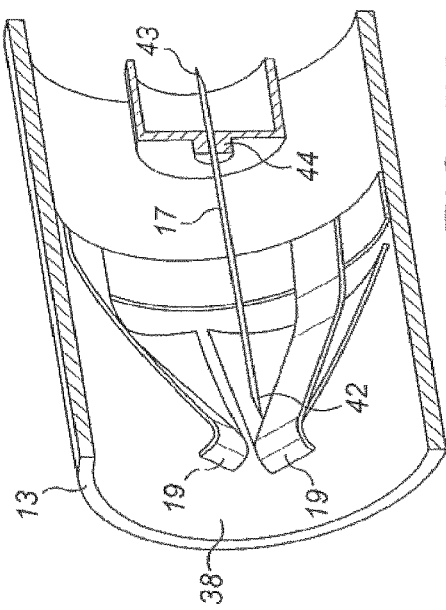
FIG. 6B shows a cross-sectional view of the part of the medicament delivery device of FIG. 6A.
Figure 7A:
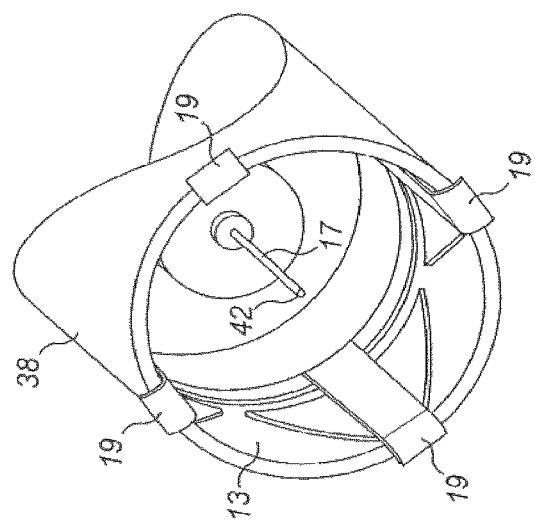
FIG. 7A shows a perspective view of a part of the medicament delivery device of FIG. 1A showing in greater detail the shield arms in the needle safe position.
Figure 7B:
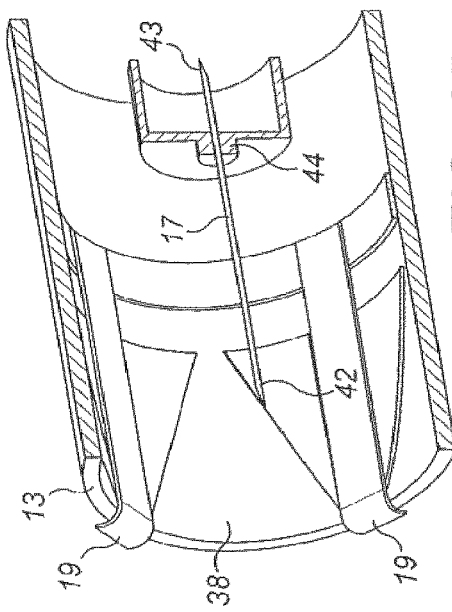
FIG. 7B shows a cross-sectional view of the part of the medicament delivery device of FIG. 7A.

The injection needle 17 is in the form of a hollow needle 17 comprising a proximal end 42, a distal end 43, and an intermediate section 44 joining the proximal end 42 and the distal end 43 together. The needle 17 is moveable from a storage position (FIG. 2) towards a use position (FIGS. 3 to 5). In the storage position, the distal end 43 of the needle 17 is spaced from the cartridge 15 so that medicament cannot be delivered. In the use position, the distal end 43 of the needle 17 is inserted in the cartridge 15 so that medicament can flow from the cartridge 15 through the needle 17 to be injected to a patient's body.

The needle holder 39 comprises a needle supporting portion 45 and a flange 46 extending from the needle supporting portion 45. The needle supporting portion 45 is secured to the intermediate section 44 of the needle 17 and supports the needle 17 in a position substantially parallel to the longitudinal axis X. The needle 17 locates in the needle holder 39 such that the flange 46 surrounds the distal end 43 of the needle 17. The flange 46 has an inner surface and an outer surface. The inner surface of the flange 46 has an internal thread 49 which is configured to mesh with the external thread 28 of the proximal portion 27 of the cartridge holder 14. The flange 46 comprises a sealing film or sealing membrane 50 which extends in the flange 46 transversally to the longitudinal axis X. The sealing membrane 50 seals the distal end 43 of the needle 17 in the flange 46 when the needle 17 is in the storage position. As will be explained in more detail below, the sealing membrane 50 is configured to be sliced by the cutting blades 32 of the cartridge holder 14 to expose the distal end 43 of the needle 17 when the needle 17 moves towards the use position.

The inner needle cap 40 surrounds the proximal end 42 of the needle 17 to protect the proximal end 42 of the needle 17 when the device 10 is not in use. The inner needle cap 40 is tubular. The diameter of the inner needle cap 40 is such that an internal surface of the inner needle cap 40 tightly abuts the needle supporting portion 45 of the needle holder 39 to securely locate the inner needle cap 40 thereon. With the inner needle cap 40 thus located, the needle 17 is fully enclosed in the inner needle cap 40.

The outer needle cap 41 locates over the inner needle cap 40 and the needle holder 39. The outer needle cap 41 is tubular having a distal section 56 and a proximal section 57. The distal section 56 locates over the outer surface of the flange 46 of the needle holder 39. The diameter of the distal section 56 is such that an internal surface of the distal section 56 tightly abuts the outer surface of the flange 46 of the needle holder 39 to securely locate the outer needle cap 41 thereon. The diameter of the proximal section 57 is smaller than the diameter of the distal section 56. The diameter of the proximal section 57 is such that an internal surface of the proximal section 57 lightly abuts an external surface of the inner needle cap 40. An external shoulder 62 is provided on the distal section 56 and extends around the entire circumference of the distal section 56.

The coupling mechanism 18 comprises a spindle 63 fixedly secured to the proximal section 57 of the outer needle cap 41 and extending along the longitudinal axis X of the housing 11. The spindle 63 comprises a first spindle section 64 and a second spindle section 65. The diameter of the first spindle section 64 is greater than the diameter of the second spindle section 65 such that a shoulder 66 is formed at the junction between the first spindle section 64 and the second spindle section 65. The first spindle section 64 is hollow and receives the proximal section 57 of the outer needle cap 41. The first spindle section 64 is fixedly attached to the proximal section 57 of the outer needle cap 41. The first spindle section 64 has a first external thread 67 having a first thread pitch. The second spindle section 65 has a second external thread 68 having a second thread pitch. The first thread pitch is smaller than the second thread pitch. For example, the ratio between the first thread pitch and the second thread pitch is comprised between 0.5 and 0.9.

The cap assembly 12 comprises an outer cap 69 and an inner cap 70. The outer cap 69 comprises an outer cap surface 71 from which extend an external cylindrical portion 72 and an internal cylindrical portion 73. The external cylindrical portion 72 has a diameter which substantially equals the diameter of the housing 11. The internal cylindrical portion 73 extends within the external cylindrical portion 72 along the longitudinal axis X. The internal cylindrical portion 73 comprises a first stop member 74 extending inwardly and circumferentially at an end 75 of the internal cylindrical portion 73 opposed to the outer cap surface 71. The first stop member 74 comprises a third thread 76 meshing with the second external thread 68 of the second spindle section 65. The inner cap 70 is substantially cylindrical and extends along the longitudinal axis X. The inner cap 70 extends within the retractable sleeve 13. The inner cap 70 has a distal end 77, a proximal end 78 and an intermediate region 79 extending between the distal end 77 and the proximal end 78. The inner cap 70 comprises a second stop member 80 extending circumferentially at the proximal end 78 of the inner cap 70, and a third stop member 81 extending circumferentially at the distal end 77 of the inner cap 70. The second stop member 80 is configured to engage the first stop member 74 of the internal cylindrical portion 73 of the outer cap 69. The third stop member 81 is configured to engage the external shoulder 62 of the distal section 56 of the outer needle cap 41. A protrusion 82 extends circumferentially and inwardly from the intermediate region 79 of the inner cap 70. The protrusion 82 comprises a fourth thread 83 meshing with the first external thread 67 of the first spindle section 64. A circumferential recess 84 is provided on an external surface of the intermediate region 79 and is configured to receive the circumferential notch 36 of the sleeve 13, so that the inner cap 70 is detachably fixed to the sleeve 13.

A gripping mechanism in the form of a catch 86 is provided at the distal end 77 of the inner cap 70. The catch 86 comprises a pair of spring arms 87 each having a first end 88 secured to the third stop member 81 of the inner cap 70 and a second end or free end 89 opposed to the first end 88. The spring arms 87 face each other. The spring arms 87 are biased towards each other. The spring arms 87 are movable between a retracted or rest position in which the second end 89 of each spring arm 87 rests on the wall 24 of the cartridge holder 14, and an engaged position in which the free end 89 of each spring arm clamp the inner needle cap 40. The spring arms 87 move from the retracted position to the engaged position when the cap assembly 12 is pulled away from the cartridge holder 14. The spring arms 87 are configured such that the second end 89 fold on and clamp or grip the inner needle cap 40 when the inner cap 70 is pulled away from the sleeve 13 to remove the inner needle cap 40 from the needle holder 39.

The shield elements 19 are distributed on an inner wall of the sleeve 13. The shield elements 19 are shown in greater detail in FIGS. 6A to 7B. The shield elements 19 are in the form of a first, second, third and fourth shield arms 19 protruding from the proximal extremity 38 of the sleeve 13. The shield arms 19 are movable between an inactive position in which the proximal end 42 of the needle 17 is exposed and a needle safe position in which access to the proximal end 42 of the needle 17 is occluded. When the inner cap 70 is attached to the sleeve 13, the shield arms 19 rest on the external surface of the inner cap 70 such that the shield arms 19 are held in the inactive position by the inner cap 70. The inner cap 70 thereby prevents the shield arms 19 from moving towards the needle safe position. The shield arms 19 are biased towards the needle safe position such that pulling the inner cap 70 away from the sleeve 13 causes the shield arms 19 to move towards a needle safe position.

The operation of the medicament injection device 10 in accordance with the present disclosure will now be described.

Initially, as shown in FIG. 2, a cartridge 15 is received in the cartridge holder 14 and the cap assembly 12 is mounted to the housing 11. The needle 17 is in the storage position, i.e. the distal end 43 of the needle 17 is spaced from the cartridge 15. The distal end 43 of the needle 17 is sealed in the flange 46 of the needle holder 39 by the sealing membrane 50, and the proximal end 42 of the needle 17 is enclosed in the inner needle cap 40. The inner needle cap 40 and the needle holder 39 locate in the outer needle cap 41. The seconds ends 89 of the spring arms 87 rest on the wall 24 of the cartridge holder 14. The notch 36 of the inner cap 70 locates in the recess 84 of the sleeve 13 such that the inner cap 70 is attached to the sleeve 13. The shield arms 19 rest on the external surface of the inner cap 70 such that the shield arms 19 are held in the inactive position by the inner cap 70.

In use, the outer cap 69 is pulled away from the cartridge holder 14, as shown by the arrow A in FIG. 3. As the third thread 76 of the first stop member 74 of the outer cap 69 meshes with the second thread 68 of the second spindle section 65, the outer cap 69 drives the spindle 63 into rotational movement about the longitudinal axis X of the housing 11, as shown by the arrow B. As the first thread 67 of the first spindle section 64 meshes with the fourth thread 83 of the protrusion 82 of the inner cap 70 and as the inner cap 70 is fixed relative to the sleeve 13, the spindle 63 is simultaneously driven into translational movement relative to the sleeve 13 towards the cartridge holder 14, as shown by the arrow C. As the needle assembly 16 is mounted to the spindle 63, the needle assembly 16 moves along with the spindle 63 towards the cartridge holder 14, such that the needle 17 moves from the storage position towards the use position. While the needle 17 moves towards the use position, the cutting blades 32 on the cartridge holder 14 slice the sealing membrane 50 such that the distal end 43 of the needle 17 is exposed. While the needle 17 moves further towards the use position, the distal end 43 of the needle 17 pierces the septum 35 of the cartridge 15 and the flange 46 of the needle holder 39 is screwed on the proximal portion 27 of the cartridge holder 14. The needle holder 39 is then secured to the cartridge holder 14 such that the needle 17 is held in the use position.

Then, as shown by the arrow D in FIG. 4, the outer cap 69 is pulled further away from the cartridge holder 14 such that the notch 36 of the sleeve 13 is removed from the recess 84 of the inner cap 70. This causes the first stop member 74 of the outer cap 69 to engage the second stop member 80 of the inner cap 70 such that the outer cap 69 pulls the inner cap 70 away from the sleeve 13. Simultaneously, the third stop member 81 at the distal end 77 of the inner cap 70 engages the external shoulder 62 of the outer needle cap 41 such that the outer needle cap 41 is pulled away from the needle holder 39. As the same time, the springs arms 87 move from the retracted position towards the engaged position i.e. the second ends 89 of the spring arms 87 slide along the cartridge holder 14, pass over the needle holder 39 and fold on and clamp the inner needle cap 40.

Then, as shown in FIG. 5, the outer cap 69 is pulled further away from the cartridge holder 14 such that the inner cap 70 is entirely detached from the sleeve 13 and removed from the housing 11. Simultaneously, the inner needle cap 40 is pulled away from the needle holder 39 in an axial direction along the longitudinal axis X. The shield arms 19 are no longer held in the inactive position by the inner cap 70 and therefore fold into the needle safe position to occlude the access to the proximal end 42 of the needle 17. The device 10 is then ready for injection.

To perform an injection, the sleeve 13 is further retracted into the housing 11 so that the proximal end 42 of the needle 17 passes the shield arms 19 and projects outside the device 10. The medicament is then injected to the patient in a well-known manner. After the injection, the sleeve 13 extends again in the deployed position so that the shield arms 19 cover the proximal end 42 of the needle 17 for safe disposal of the device 10.

In the embodiment described above, the coupling mechanism is described as comprising a spindle having threads configured to mesh with corresponding threads on the inner and outer caps. However, the disclosure is not intended to be limited to this particular type of coupling mechanism and other types of coupling mechanism are intended to fall within the scope of the disclosure, for example a coupling mechanism comprising helical gears for coupling the spindle to the outer and inner caps.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, microneedle), inhaler (e.g., nasal or pulmonary), an implantable device (e.g., drug- or API-coated stent, capsule), or a feeding system for the gastro-intestinal tract. The presently described drugs may be particularly useful with injection devices that include a needle, e.g., a hypodermic needle for example having a Gauge number of 24 or higher.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refer to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten. An example of an oligonucleotide is, for example: mipomersen sodium (Kynamro®), a cholesterol-reducing antisense therapeutic for the treatment of familial hypercholesterolemia. Examples of DPP4 inhibitors are Vildagliptin, Sitagliptin, Denagliptin, Saxagliptin, Berberine. Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigens. The antibody can be polyclonal, monoclonal, recombinant, chimeric, de-immunized or humanized, fully human, non-human, (e.g., murine), or single chain antibody. In some embodiments, the antibody has effector function and can fix a complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

The invention claimed is:

1. A medicament delivery device comprising:
   a cartridge holder configured for an injection needle holder to be fixed thereto, the injection needle holder being configured to hold an injection needle having a proximal end and a distal end, the proximal end being protected by an inner injection needle cap detachably connected to the injection needle holder, the cartridge holder being mounted in a housing and configured to receive a cartridge of medicament;
   a cap assembly detachably connected to the housing; and
   a gripping mechanism configured to remove the inner injection needle cap from the injection needle holder when the cap assembly is pulled away from the cartridge holder,
   wherein an outer injection needle cap is located over the inner injection needle cap, the outer injection needle cap comprising a proximal section and a distal section, wherein the proximal section is relatively closer to a site of injection than the distal section,
   wherein the cap assembly comprises a stop member, the stop member being configured to engage the distal section of the outer injection needle cap to remove the outer injection needle cap from the inner injection needle cap prior to the removal of the inner injection needle cap from the injection needle holder when the cap assembly is pulled away from the cartridge holder; and
   wherein the stop member is configured to engage the distal section of the outer injection needle cap at a location distal of a proximal end of the injection needle.

2. The medicament delivery device according to claim 1, wherein the cap assembly is configured to pull the inner injection needle cap away from the injection needle holder in an axial direction along a longitudinal axis of the housing when the cap assembly is pulled away from the cartridge holder.

3. The medicament delivery device according to claim 1, wherein the gripping mechanism comprises at least one gripping member configured to be movable from a retracted position towards an engaged position in which the at least one gripping member engages the inner injection needle cap, and wherein the at least one gripping member is configured to move from the retracted position towards the engaged position when the cap assembly is pulled away from the cartridge holder.

4. The medicament delivery device according to claim 3, wherein the at least one gripping member is configured to move relative to the cap assembly from the retracted position towards the engaged position.

5. The medicament delivery device according to claim 3, wherein the at least one gripping member comprises multiple gripping members, wherein each gripping member of the multiple gripping members comprises a spring arm having a free end, wherein the spring arms of the gripping members are configured such that the free ends of the spring arms fold on and clamp the inner injection needle cap when the cap assembly is pulled away from the cartridge holder.

6. The medicament delivery device according to claim 5, wherein in the retracted position, the free end of each spring arm of the spring arms is configured to rest on the cartridge holder, and wherein in the engaged position, the free end of each spring arm of the spring arms is configured to clamp the inner injection needle cap.

7. The medicament delivery device according to claim 5, wherein the spring arms are biased towards each other.

8. The medicament delivery device according to claim 3, wherein a first end of the at least one gripping member is secured to the stop member.

9. The medicament delivery device according to claim 1, wherein the cap assembly comprises the inner injection needle cap and the outer injection needle cap connected to the inner injection needle cap.

10. The medicament delivery device according to claim 1, wherein the gripping mechanism comprises a catch configured to hold the inner injection needle cap and remove the inner injection needle cap from the injection needle holder when the cap assembly is pulled away from the cartridge holder.

11. The medicament delivery device according to claim 1, further comprising the cartridge of medicament, the cartridge of medicament being received in the cartridge holder.

12. The medicament delivery device according to claim 1, wherein the outer injection needle cap comprises an external shoulder, and wherein the stop member is configured to engage the external shoulder.

13. The medicament delivery device according to claim 1, wherein the outer injection needle cap is configured to tightly abut a part of the injection needle holder.

14. The medicament delivery device according to claim 1, wherein the injection needle holder comprises a flange and wherein the outer injection needle cap is configured to locate over the flange.

15. The medicament delivery device according to claim 1, wherein the inner injection needle cap and the injection needle holder are configured to locate in the outer injection needle cap.

16. The medicament delivery device according to claim 1, wherein the injection needle is movable from a storage position to a use position, wherein in the storage position, the distal end of the injection needle is spaced from the cartridge of medicament and, in the use position, the distal end of the injection needle is inserted in the cartridge of medicament.

17. A method of removing an inner injection needle cap from an injection needle in a medicament delivery device, the method comprising:
moving a cap assembly of the medicament delivery device a predetermined distance in a proximal direction to remove the cap assembly and the inner injection needle cap from the medicament delivery device, wherein an outer injection needle cap is located over the inner injection needle cap, the outer injection needle cap comprising a proximal section and a distal section, wherein the proximal section is relatively closer to a site of injection than the distal section, and wherein the cap assembly comprises a stop member configured to engage a distal section of the outer injection needle cap at a location distal of a proximal end of the injection needle to remove the outer injection needle cap from the inner injection needle cap prior to the removal of the inner injection needle cap from an injection needle holder when the cap assembly is moved in the proximal direction.

18. The method according to claim 17, wherein moving the cap assembly the predetermined distance causes the outer injection needle cap to be removed from the inner injection needle cap.

19. The method according to claim 17, wherein the method further comprises moving the injection needle from a storage position to a use position, wherein in the storage position, the distal end of the injection needle is spaced from a cartridge of medicament and, in the use position, the distal end of the injection needle is inserted in the cartridge of medicament.

* * * * *